US012718908B2

(12) United States Patent
Kuznetsov et al.

(10) Patent No.: US 12,718,908 B2
(45) Date of Patent: Aug. 25, 2026

(54) GRAPH NORMALIZING FLOW FOR HIERARCHICAL MOLECULAR GENERATION

(71) Applicant: Insilico Medicine IP Limited, Hong Kong (HK)

(72) Inventors: Maksim Kuznetsov, Moscow (RU); Daniil Polykovskiy, Moscow (RU); Aleksandrs Zavoronkovs, Pak Shek Kok (HK)

(73) Assignee: INSILICO MEDICINE IP LIMITED, Hong Kong (HK)

( * ) Notice: Subject to any disclaimer, the term of this patent is extended or adjusted under 35 U.S.C. 154(b) by 1188 days.

(21) Appl. No.: 17/331,493

(22) Filed: May 26, 2021

(65) Prior Publication Data

US 2021/0383898 A1 Dec. 9, 2021

Related U.S. Application Data

(60) Provisional application No. 63/035,546, filed on Jun. 5, 2020.

(51) Int. Cl.

*G06F 30/27* (2020.01)
*G16C 20/50* (2019.01)
*G16C 20/70* (2019.01)
*G16C 20/80* (2019.01)

(52) U.S. Cl.

CPC ............. *G16C 20/50* (2019.02); *G06F 30/27* (2020.01); *G16C 20/70* (2019.02); *G16C 20/80* (2019.02)

(58) Field of Classification Search

CPC ........ G16C 20/50; G16C 20/70; G16C 20/80; G06F 30/27; G06N 3/045; G06N 3/047; G06N 3/08; G06N 5/01

See application file for complete search history.

(56) References Cited

PUBLICATIONS

Jin, Wengong, et al. "Learning multimodal graph-to-graph translation for molecular optimization." arXiv preprint arXiv:1812.01070 (2018) (Year: 2018).*
Dinh, Laurent et al. "Density estimation using Real NVP." ArXiv abs/1605.08803 (2016) (Year: 2016).*
Schneider, Gisbert. "Automating drug discovery." Nature Reviews Drug Discovery 17.2 (2018) (Year: 2018).*
Mitchell, John BO. "Machine learning methods in chemoinformatics." Wiley Interdisciplinary Reviews: Computational Molecular Science 4.5 (2014): 468-481 (Year: 2014).*
Segler et al. "Planning chemical syntheses with deep neural networks and symbolic AI" Nature 555, 604-610 (2018), https://doi.org/10.1038/nature25978.
Senior et al. "Improved protein structure prediction using potentials from deep learning" Nature 577, 706-710 (2020) https://doi.org/10.1038/s41586-019-1923-7.
Merk et al. "De Novo Design of Bioactive Small Molecules by Artificial Intelligence" Molecular Informatics, vol. 37 Issue 1-2, Special Issue: Generative Models, Jan. 10, 2018, DOI: 10.1002/minf.201700153.
Zhavoronkov et al. "Deep learning enables rapid identification of potent DDR1 kinase inhibitors" Nat Biotechnol 37, 1038-1040 (2019). https://doi.org/10.1038/s41587-019-0224-x.
Polykovskiy et al. "Molecular Sets (MOSES): A Benchmarking Platform for Molecular Generation Models" Front. Pharmacol., Dec. 18, 2020 https://doi.org/10.3389/fphar.2020.565644.
Brown et al. "GuacaMol: Benchmarking Models for de Novo Molecular Design" Journal of Chemical Information and Modeling 2019 59, 1096-1108, DOI: 10.1021/acs.jcim.8b00839.
Gomez-Bombarelli et al. "Automatic Chemical Design Using a Data-Driven Continuous Representation of Molecules" ACS Central Science 2018 4, 268-276 DOI: 10.1021/acscentsci.7b00572.
Dinh et al. "Density Estimation Using Real NVP" International Conference on Learning Representations, 2017, arXiv:1605.08803v3 [cs.LG] Feb. 27, 2017.
Kingma et al. "Glow: Generative Flow with Invertible 1×1 Convolutions" Advances in Neural Information Processing Systems, pp. 10215-10224, 2018.
Velickovic et al. "Graph Attention Networks" International Conference on Learning Representations, 2017.
Guo et al. "Attention guided graph convolutional networks for relation extraction" Proceedings of the 57th Annual Meeting of the Association for Computational Linguistics, pp. 241-251, Florence, Italy, Jul. 2019.
Vaswani et al. "Attention is all you need" Advances in neural information processing systems, pp. 5998-6008, 2017.
Parisotto et al., "Stabilizing transformers for reinforcement learning" International Conference on Machine Learning, 2020.
Degen et al., "On the art of compiling and using 'drug-like' chemical fragment spaces" ChemMedChem, 3(10):1503-1507, 2008 DOI: 10.1002/cmdc.200800178.

(Continued)

*Primary Examiner* — Soren Harward
*Assistant Examiner* — Dawn Bickham
(74) *Attorney, Agent, or Firm* — MASCHOFF BRENNAN

(57) ABSTRACT

A computing method for normalizing molecule graph data for hierarchical molecular generation can include: providing molecule graph data of a molecule having a node; recursively splitting the node into two nodes; iteratively recursively spilling other nodes into two nodes; generating generated molecular graph data of a generated molecule from node splitting; and providing a report with the generated molecular graph. A computing method can include: providing molecule graph data into a latent code generator having multiple levels with a forward and inverse; and generating latent codes by processing molecule graph data through multiple levels of operations, wherein each level of operations has a sequence of sublevels of operations in forward path and inverse path, wherein the sublevels of operations include node merging operation and node splitting operation; generating at least one molecular structure from latent codes; and outputting generate molecule graph data having the at least one molecular structure.

21 Claims, 8 Drawing Sheets

(56) References Cited

PUBLICATIONS

Bemis et al., "The properties of known drugs. 1. molecular frameworks" J. Med. Chem. 1996, 39, 15, 2887-2893 https://doi.org/10.1021/jm9602928.
Segler et al., "Generating focused molecule libraries for drug discovery with recurrent neural networks" ACS Cent. Sci. 2018, 4, 1, 120-131 Dec. 28, 2017 https://doi.org/10.1021/acscentsci.7b00512.
Sanchez-Lengeling et al., "Optimizing distributions over molecular space. An Objective-Reinforced Generative Adversarial Network for Inverse-design Chemistry (ORGANIC)" ChemRxiv, Aug. 2017. doi: 10.26434/chemrxiv.5309668.v3.
Kusner et al., "Grammar variational autoencoder" In Proceedings of the 34th International Conference on Machine Learning—vol. 70, pp. 1945-1954. JMLR. org, 2017.
Noel O'Boyle et al., "DeepSMILES: An Adaptation of SMILES for Use in Machine-Learning of Chemical Structures" ChemRxiv, 2018 Preprint. https://doi.org/10.26434/chemrxiv.7097960.v1.
Krenn et al., "Selfies: a robust representation of semantically constrained graphs with an example application in chemistry" arXiv preprint arXiv:1905.13741, 2019.
Preuer, et al., "Frechet ChemNet distance: A metric for generative models for molecules in drug discovery" J. Chem. Inf. Model., 58(9):1736-1741, Sep. 2018 https://doi.org/10.1021/acs.jcim.8b00234.
Jin et al., "Junction tree variational autoencoder for molecular graph generation" Proceedings of the 35th International Conference on Machine Learning, PMLR 80:2323-2332, 2018.
Hoogeboom et al., "Emerging convolutions for generative normalizing flows" Proceedings of the 36th International Conference on Machine Learning, vol. 97 of Proceedings of Machine Learning Research, pp. 2771-2780, Long Beach, California, USA, Jun. 9-15, 2019.
International Search Report and Written Opinion for PCT/IB2021/054619 mailed Jul. 29, 2021.
Kuznetsov, Maksim and Daniil Polykovskiy. "MolGrow: A Graph Normalizing Flow for Hierarchical Molecular Generation." AAAI (2021).
Xia et al. "Graph-based generative models for de Novo drug design" Drug Discovery Today: Technologies vols. 32-33, Dec. 2019, pp. 45-53.
Shi et al. "GraphAF: a Flow-based Autoregressive Model for Molecular Graph Generation" Cornell University Library Jan. 26, 2020, arXiv:2001.09382.

* cited by examiner

| Algorithm 1. Attention on complete graph edges (CAGE) |
|---|
| Input: Complete graph $(V, E)$ with node feature matrix $V \in R^{n \times d_v}$ and edge feature tensor $E \in R^{n \times n \times d_e}$ |
| Output: Transformed complete graph $(V, E)$ of the same dimension as $(V, E)$ |
| 1: Compute positional encodings matrix pos $\in R^{n \times d_v}$ |
| 2: for $i = 1$ to $n$ do |
| 3: Allocate $\mu \in R^{n \times d_v}$ |
| 4: for $j = 1$ to $n$ do |
| 5: $\mu_j = f_\theta\left(\text{cat}(E_{i,j}, V_i, V_j)\right) + \text{pos}_j$ — compute message $j \rightarrow i$ of dimension $d_v$ using a fully-connected neural network $f_\theta$ |
| 6: end for |
| 7: $q = V_i + \text{pos}_i$— compute attention query |
| 8: $r = \text{Multi–Head Attention}(\text{query} = q, \text{keys} = \mu, \text{values} = \mu)$ — aggregate messages |
| 9: $\overline{V}_i = \text{GRU}_V(x = r, h = V_i)$ — update node |
| feature matrix using a GRU cell<br>10: $\nu_{i,j} = \text{cat}(E_{i,j}, \overline{V}_i, \overline{V}_j), \forall j$— compute edge update vectors |
| 11: $\overline{E}_{i,j} = \frac{1}{2}\text{GRU}_E(x = \nu_{i,j}, h = E_{i,j}) + \frac{1}{2}\text{GRU}_E(x = \nu_{j,i}, h = E_{j,i}), \forall j$— update edge features |
| 12: end for |

Fig. 5B

| Algorithm 2. Balanced padding (function "pad") |
| --- |
| Input: List of fragments $f_{1:K} = [f_1 \dots f_K]$, where $f_i$ contains atom indices in the $i$-th fragment; $N$- target graph size, power of 2. |
| Output: Atom order with $*$ indicating padding positions ($*_N$ indicates $N$ sequential paddings). |
| 1:If $K = 1$ and $\lvert f_1 \rvert \leq N/2$ then |
| 2: Randomly add padding: with 50% probability return $\mathrm{cat}\left(\mathrm{pad}(f_1, N/2), *_{N/2}\right)$, otherwise return $\mathrm{cat}\left(*_{N/2}, \mathrm{pad}(f_1, N/2)\right)$ |
| 3:end if |
| 4:Find possible splitting positions $B$: $b \in B$ if left and right parts fit into subtrees: $\lvert f_{1:b} \rvert \leq N/2$ and $\lvert f_{b+1:K} \rvert \leq N/2$ |
| 5:if $\lvert B \rvert > 0$ then |
| 6: Sample any index $b \in B$ that minimizes the number of bonds between $f_{1:b}$ and $f_{b+1:K}$. |
| 7: Recursively add padding to left and right parts: |
| 8: return $\mathrm{cat}\left(\mathrm{pad}(f_{1:b}, N/2), \mathrm{pad}(f_{b+1:K}, N/2)\right)$ |
| 9:else |
| 10: Add padding to the right |
| 11: return $\mathrm{cat}\left(f_{1:K}, *_{N-\lvert f_{1:K} \rvert}\right)$ |
| 12:end if |

Fig. 8

GRAPH NORMALIZING FLOW FOR HIERARCHICAL MOLECULAR GENERATION

CROSS-REFERENCE TO RELATED APPLICATIONS

This patent application claims priority to U.S. Provisional Application No. 63/035,546 filed Jun. 5, 2020, which provisional is incorporated herein by specific reference in its entirety.

BACKGROUND

Field

The present disclosure relates to computing methods for normalizing graph data for hierarchical molecular generation.

Description of Related Art

Drug discovery is a challenging multidisciplinary task that combines domain knowledge in chemistry, biology, and computational science. Recent works demonstrated successful applications of machine learning to the drug development process, including synthesis planning [Marwin H S Segler et al. Planning chemical syntheses with deep neural networks and symbolic ai. *Nature,* 555(7698):604-610, 2018.], protein folding [Andrew W Senior et al. Improved protein structure prediction using potentials from deep learning. *Nature, pages* 1-5, 2020.], and hit discovery [Daniel Merk et al.. De novo design of bioactive small molecules by artificial intelligence. *Molecular informatics,* 37(1-2): 1700153, 2018; and Alex Zhavoronkov et al., Deep learning enables rapid identification of potent DDR1 kinase inhibitors. *Nature biotechnology, pages* 1-4, 2019]. Advances in generative models enabled applications of machine learning to drug discovery, such as distribution learning and molecular property optimization. Distribution learning models train on a large dataset to produce novel compounds [Daniil Polykovskiy et al., Molecular sets (MOSES): A benchmarking platform for molecular generation models. *Frontiers in Pharmacology,* 11:1931, 2020]; property optimization models search the chemical space for molecules with desirable properties [Nathan Brown et al., Guacamol: benchmarking models for de novo molecular design. *Journal of chemical information and modeling,* 59(3):1096-1108, 2019]. Often researchers combine these tasks: they first train a distribution learning model and then use its latent codes to optimize molecular properties [Rafael Gomez-Bombarelli, Automatic chemical design using a Data-' Driven continuous representation of molecules. *ACS Central Science,* 4(2):268-276, February 2018]. For such models, proper latent codes are crucial for molecular space navigation.

SUMMARY

In some embodiments, a computing method for normalizing molecule graph data for hierarchical molecular generation can include: providing molecule graph data of at least one molecule having a node; recursively splitting the node into two nodes; iteratively recursively spilling other nodes in the molecular graph data into two nodes; generating generated molecular graph data of a generated molecule from node splitting; and providing a report with the generated molecular graph of the generated molecule. In some aspects, the method can include iteratively merging two nodes into a single node. In some aspects, the method can include perturbating a first layer of latent code to obtain a global structural change of at least one resulting molecule of the generated molecular graph. In some aspects, the method can include perturbating one or more consequent layers to change at least one resulting molecule in one or more changes to a scaffold or substituent of the at least one resulting molecule to obtain a generated molecular graph.

In some embodiments, the molecular graph data includes a single node graph data, and the generated molecular graph includes a multi node graph data. In some aspects, the method uses node merging and node splitting to control size of the generated molecule graph.

In some embodiments, the method includes performing a fragment-oriented atom ordering that improves hierarchical normalizing flow of a model over breadth-first search ordering.

In some embodiments, the method includes mapping a molecular structure of molecular graph data onto a fixed-sized hierarchical manifold.

In some embodiments, the method includes transforming a prior distribution into a target distribution through invertible functions having a forward path and an inverse path. In some aspects, the prior distribution is a standard multivariate normal distribution of molecular graph data; and the target distribution includes the generated molecular graph data.

In some embodiments, the method can include processing molecular graph data through a plurality of levels of operations to generate latent codes in each level of operations in a forward path and/or an inverse path. In some aspects, each level of operations performs a sequence of sublevels of operations in a forward path and an inverse path, wherein the sublevels of operations include at least: noise injection operation; noise separation operation; a node merging operation; a node splitting operation; a plurality of block operations; actnorm transformation; linear transformation; and permutation transformation. In some aspects, each sublevel of operations performs a sequence of operations in a forward path and an inverse path, each block operation includes at least: permutation transformation; linear transformation; actnorm transformation; first real-valued non-volume preserving transformation; and second real-valued non-volume preserving transformation.

In some embodiments, the linear transformation includes an invertible linear transformation, and a decomposition of a weight matrix with an orthogonal matrix and an upper triangular matrix with ones on the main diagonal. In some aspects, the actnorm transformation includes a linear transformation with a diagonal weight matrix. In some aspects, the first and second real-valued non-volume preserving transformation are sequentially applied as nonlinear invertible transformations. In some aspects, the permutation transformation deterministically shuffles input dimensions or randomly splits data into two separate parts.

In some embodiments, each forward path level extracts the latent code and halves its graph size by merging node pairs. In some aspects, each inverse path level splits each node into two nodes and adds additional noise. In some aspects, the forward path provides output as a single node graph and latent codes for each level.

In some embodiments, the method includes performing a dequantization with uniform noise, wherein data for each training batch is independently dequantized, and the model is trained on a complete graph.

In some embodiments, the method includes producing a latent vector for each level by: deriving latent codes by separating half of node and edge features before node merging; imposing a Gaussian prior on the derived latent codes; and sampling the latent code from the Gaussian prior and concatenating the latent code with node and edge features.

In some embodiments, the method is performed in a distribution learning and property optimization task. In some aspects, the method includes providing a report that includes distribution learning metrics or graph generative models.

In some embodiments, the method includes: transforming the molecule graph into nodes and edges; transforming the nodes and edges by projecting node and edge features onto a low-dimensional manifold; applying fully-connected neural networks to each node and edge independently; and performing an attentive graph convolution.

In some embodiments, the method includes: splitting the molecule graph data into fragments; for each fragment, select an atom with a minimal breadth-first-search (BFS) index in an original molecule and sort the fragments according to indices; perform a BFS for selected atoms to order atoms in each fragment; obtain an ordered list of fragments and ordered list of atoms for each fragment; and concatenate the ordered list of fragments to obtain a final ordering.

In some embodiments, a method of generating a molecule can include: performing the method of one of the embodiments to identify a molecular structure of the generated molecule; and synthesizing a real molecule to have the molecular structure.

In some embodiments, a computing method for normalizing molecule graph data for hierarchical molecular generation can include: providing molecule graph data into a latent code generator having multiple levels with a forward path and an inverse path; and generating latent codes by processing the molecule graph data through multiple levels of operations, wherein each level of operations has a sequence of sublevels of operations in the forward path and inverse path, wherein the sublevels of operations include at least a node merging operation and a node splitting operation; generating at least one molecular structure from latent codes; and outputting generate molecule graph data having the at least one molecular structure. In some aspects, the method includes processing molecular graph data through a plurality of levels of operations to generate latent codes in each level of operations in a forward path and/or an inverse path. In some aspects, each level of operations performs a sequence of sublevels of operations in a forward path and an inverse path, wherein the sublevels of operations include at least: noise injection operation; noise separation operation; a node merging operation; a node splitting operation; a plurality of block operations; actnorm transformation; linear transformation; and permutation transformation. In some aspects, each sublevel of operations performs a sequence of operations in a forward path and an inverse path, each block operation includes at least: permutation transformation; linear transformation; actnorm transformation; first real-valued non-volume preserving transformation; and second real-valued non-volume preserving transformation. In some aspects, the linear transformation includes an invertible linear transformation, and a decomposition of a weight matrix with an orthogonal matrix and upper triangular matrix with ones on the main diagonal. In some aspects, the actnorm transformation includes a linear transformation with a diagonal weight matrix. In some aspects, the first and second real-valued non-volume preserving transformation are sequentially applied as nonlinear invertible transformations. In some aspects, the permutation transformation deterministically shuffles input dimensions or randomly splits data into two separate parts. In some aspects: each forward path level extracts the latent code and halves its graph size by merging node pairs; and each inverse path level splits each node into two nodes and adds additional noise.

In some embodiments, one or more non-transitory computer readable media are provided that store instructions that in response to being executed by one or more processors, and cause a computer system to perform operations, the operations comprising the computer method of one of the embodiments.

In some embodiments, a computer system can include: one or more processors; and one or more non-transitory computer readable media storing instructions that in response to being executed by the one or more processors, cause the computer system to perform operations, the operations comprising the computer method of one of the embodiments.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 5B illustrates an algorithm for applying attention on complete graph edges (CAGE) architecture.

FIG. 8 illustrates an Algorithm for applying balanced padding.

Figure 1:
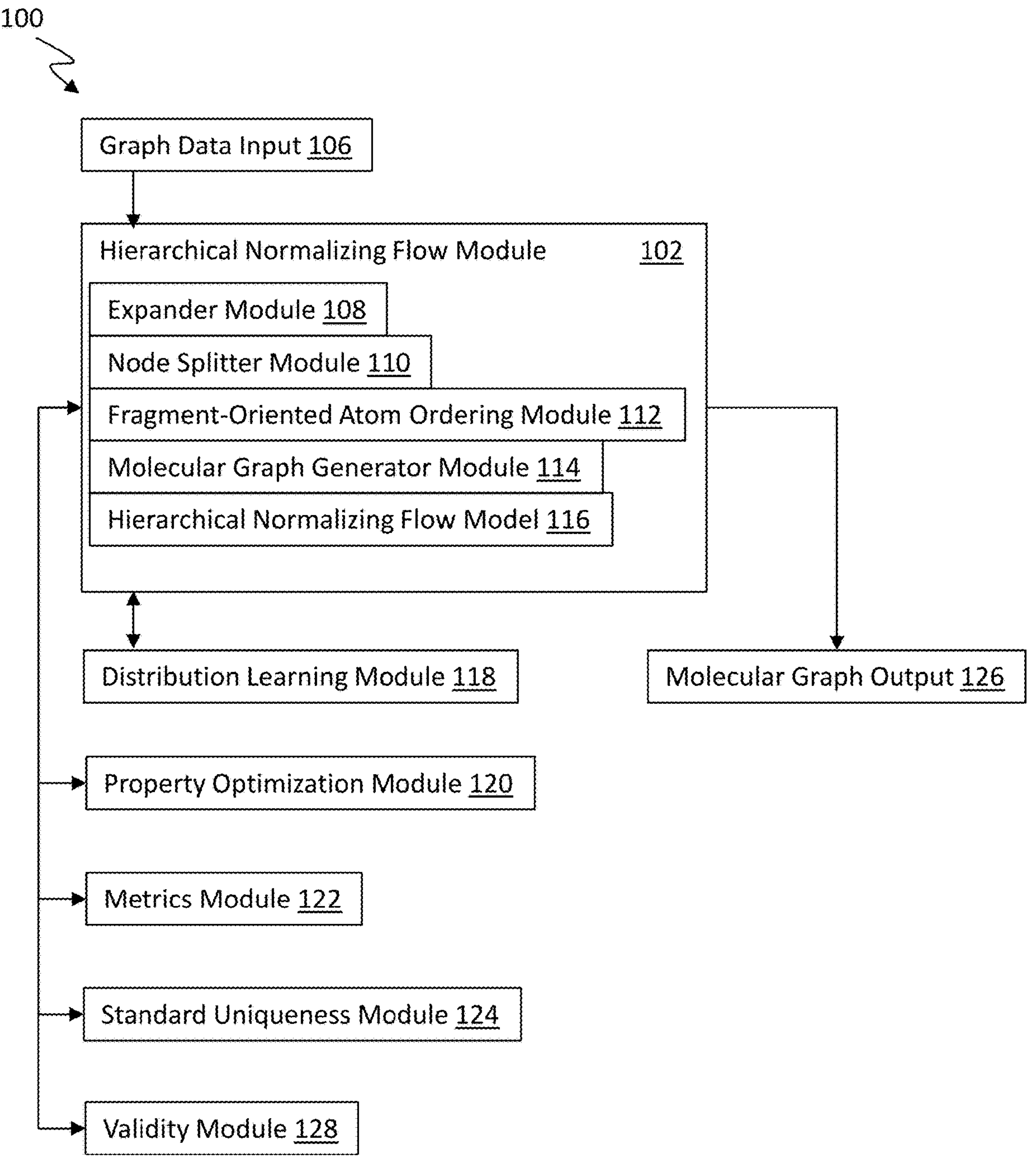
FIG. 1 shows an architecture of a system having a hierarchical normalizing flow module that is configured for generating molecular graphs.

The elements and components in the figures can be arranged in accordance with at least one of the embodiments described herein, and which arrangement may be modified in accordance with the disclosure provided herein by one of ordinary skill in the art.

DETAILED DESCRIPTION

In the following detailed description, reference is made to the accompanying drawings, which form a part hereof In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present technology is related to a hierarchical normalizing flow model for generating molecular graphs. The hierarchical normalizing flow model is configured to produce new molecular structures from a single-node graph by recursively splitting every node into two nodes. All operations in the hierarchical normalizing flow model are invertible and can be used as plug-and-play modules. The hierarchical nature of the latent codes allows for precise changes in the resulting graph. For example, perturbations in the top layer cause global structural changes, while perturbations in the consequent layers change the resulting molecule marginally. The proposed hierarchical normalizing flow model outperforms existing generative graph models on the distribution learning task. The hierarchical normalizing flow model can be used for global and constrained optimization of chemical properties using latent codes of the model.

In some embodiments, the hierarchical normalizing flow model for generating molecular graphs can be used as a graph generative model, and thereby can be referred to as "MolGrow." The hierarchical normalizing flow model can start with a single node and then iteratively split that node and then ever other node in the molecular graph into two nodes. The hierarchical normalizing flow model for generating molecular graphs model is invertible and can be used to map molecular structures onto a fixed-size hierarchical manifold. The top levels of the manifold are configured to define global structure, while the bottom levels influence local features.

In some embodiments, the hierarchical normalizing flow model can be used for generating molecular graphs. The model is configured so that it gradually increases graph size during sampling, starting with a single node. The node can be split into two nodes. Then, each node can be processed and split into two nodes.

In some embodiments, the hierarchical normalizing flow model can be used with a fragment-oriented atom ordering (e.g., hierarchical ordering) that improves the hierarchical normalizing flow model over commonly used breadth-first search ordering.

In some embodiments, the hierarchical normalizing flow model can be applied to distribution learning and property optimization tasks. The hierarchical normalizing flow model can provide a report that includes distribution learning metrics (e.g., Frechet ChemNet distance and fragment distribution) for graph generative models besides providing standard uniqueness and validity measures.

FIG. 1 shows an architecture of a system 100 having a hierarchical normalizing flow module 102 that is configured for generating molecular graphs with a molecular graph generator module 114. The module 102 can include a graph data input 106 and a graph data expander module 108 that is configured for gradually increases graph size of a graph in the graph data during a sampling protocol. The graph data expander module 108 can begin the graph size increase protocol starting with a single node of the graph that is split into two child nodes with a node splitter module 110. The process can be repeated by the node splitter module 110 for the nodes of the graph. The module 102 can also include a fragment-oriented atom ordering module 112, which is configured for atom ordering (e.g., node ordering) in the graph data that improves the operation of the model in the module 102 over commonly used breadth-first search ordering. The module 102 can omit a breadth-first search ordering module. The module 102 also include a molecular graph generator module 114 configured to generate molecular graphs.

The hierarchical normalizing flow model 116 of the module 102 can be applied to a distribution learning module 118 that performs distribution learning tasks with the model 116 on the graph data and generated graph data. Also, the hierarchical normalizing flow model 116 of the module 102 can be applied to a property optimization module 120 that performs property optimization tasks.

The system 100 can include a metrics module 122 that is configured for determining the metrics of any of the module, such from the distribution learning metrics of the module 118. The metric module 122 can generate a report of the distribution learning metrics, such as Frechet ChemNet distance metrics and fragment distribution metrics for graph generative models. The system 100 can also include standard uniqueness module 124 that is configured for analyzing generated graph data that is output (e.g., from molecular graph output 126 that outputs molecular graphs 126) from the module 102. The system 100 can include a validity module 128 that is configured to validate any generated molecular graph, and thereby provide validity measures of the output molecular graphs. For example, the validity module 128 can be configured to provide a report on whether or not the molecular graph represents a valid molecule.

Figure 2:
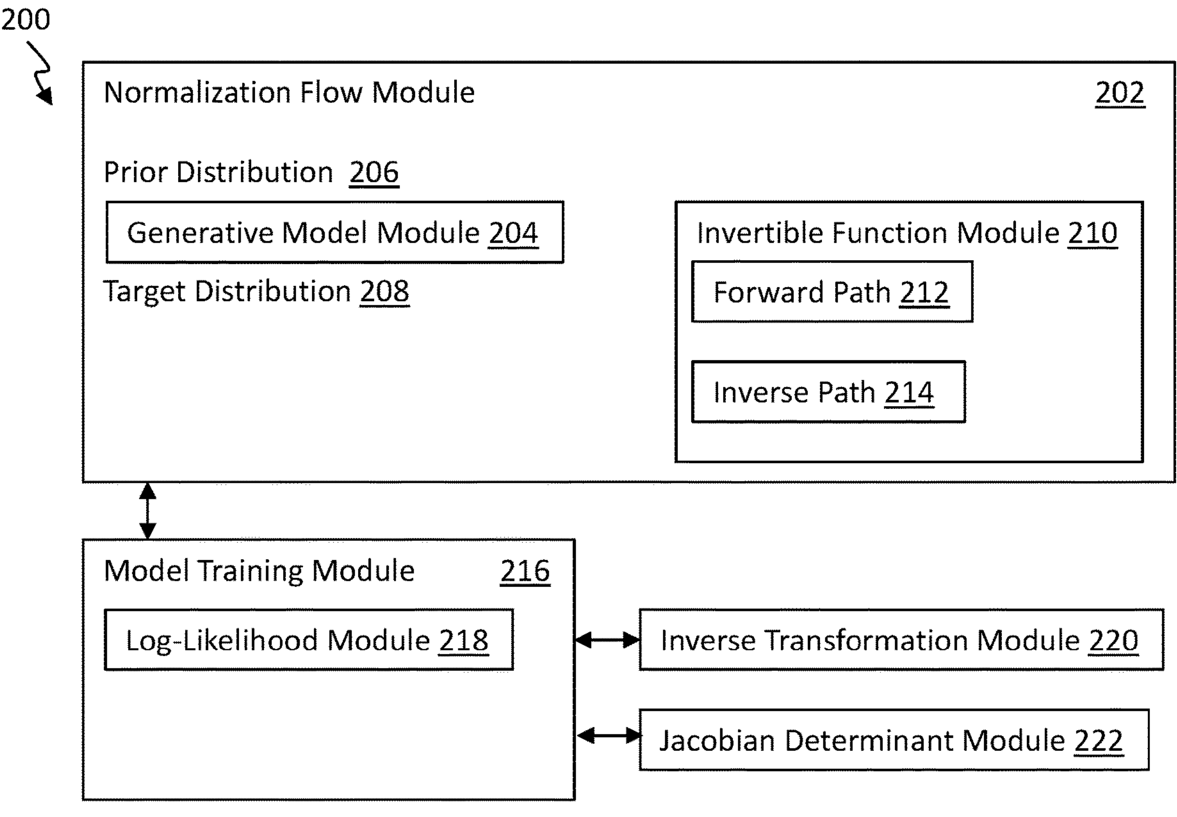
FIG. 2 illustrates a normalizing flow system transforming a prior distribution to a target distribution.

FIG. 2 illustrates a normalizing flow system 200 transforming a prior distribution 206 to a target distribution 208. The normalizing flow system 200 can include a normalizing flow module 202 that is configured with a generative module 204 that performs a transformation of the prior distribution 206 to the target distribution 208. The invertible function module 210 is configured for composing the invertible functions with a forward path 212 and an inverse path 214. For example, the prior distributionp(z) is often a standard multivariate normal distribution N(0,I). The normalizing flow models are trained with a model training module 216. The model training module 216 can include a log-likelihood module 218 that is configured for maximizing training set log-likelihood using a change of variables formula. The training module 216 can also implement training of the model through an inverse transformation module 220 and a Jacobian determinant module 222. This can ensure the inverse transformations and Jacobian determinants should be tractable and computationally efficient.

Figure 3:
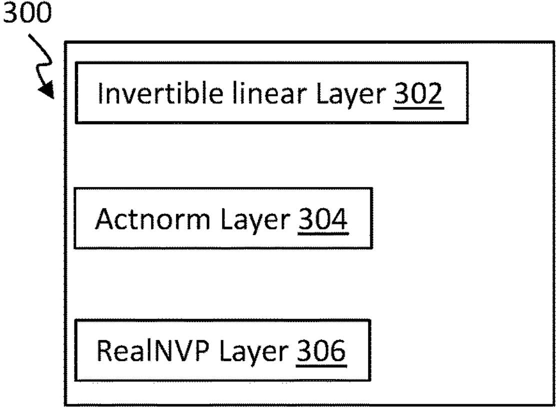
FIG. 3 illustrates a system architecture with three types of layers for obtaining the target distribution.

FIG. 3 illustrates a system architecture 300 with three types of layers for obtaining the target distribution. The three types of layers include: invertible linear layer 302, actnorm layer 304, and real-valued non-volume preserving transformation (RealNVP) layer 306 (Laurent Dinh et al., Density estimation using RealNVP. *International Conference on Learning Representations*, 2017.). These layers can include arbitrarily dimensioned vectors. Additionally, these layers can be extended for graph-structured data (e.g., graph data).

The invertible linear layer 302 is configured for performing a parameterization that uses a QR decomposition of a weight matrix. A householder reflections computation is used to parameterize an orthogonal matrix. The Jacobian determinant of the invertible linear layer 302 should be 1.

The actnorm layer 304 is a linear layer with a diagonal weight matrix. Vectors are initialized so that the output activations from the actnorm layer 304 have zero mean and unit variance at the beginning of training. A first training batch can be used for initialization. The Jacobian determent of the actnorm layer 304 can also be computed.

The RealNVP layer 306 is a nonlinear invertible transformation layer. The RealNVP considers a vector of length with half of the compounds (molecular graphs) being an A part and half of the compounds being a B part. The RealNVP transformation and its inverse transformation can be determined, and are usually in the form of a neural network. In practice, two RealNVP layers 306 are applied to transform both components of the vector. A permutation layer can be included to deterministically shuffle input dimensions before RealNVP, which is similar to randomly splitting data into the A part and B part.

Figure 4:
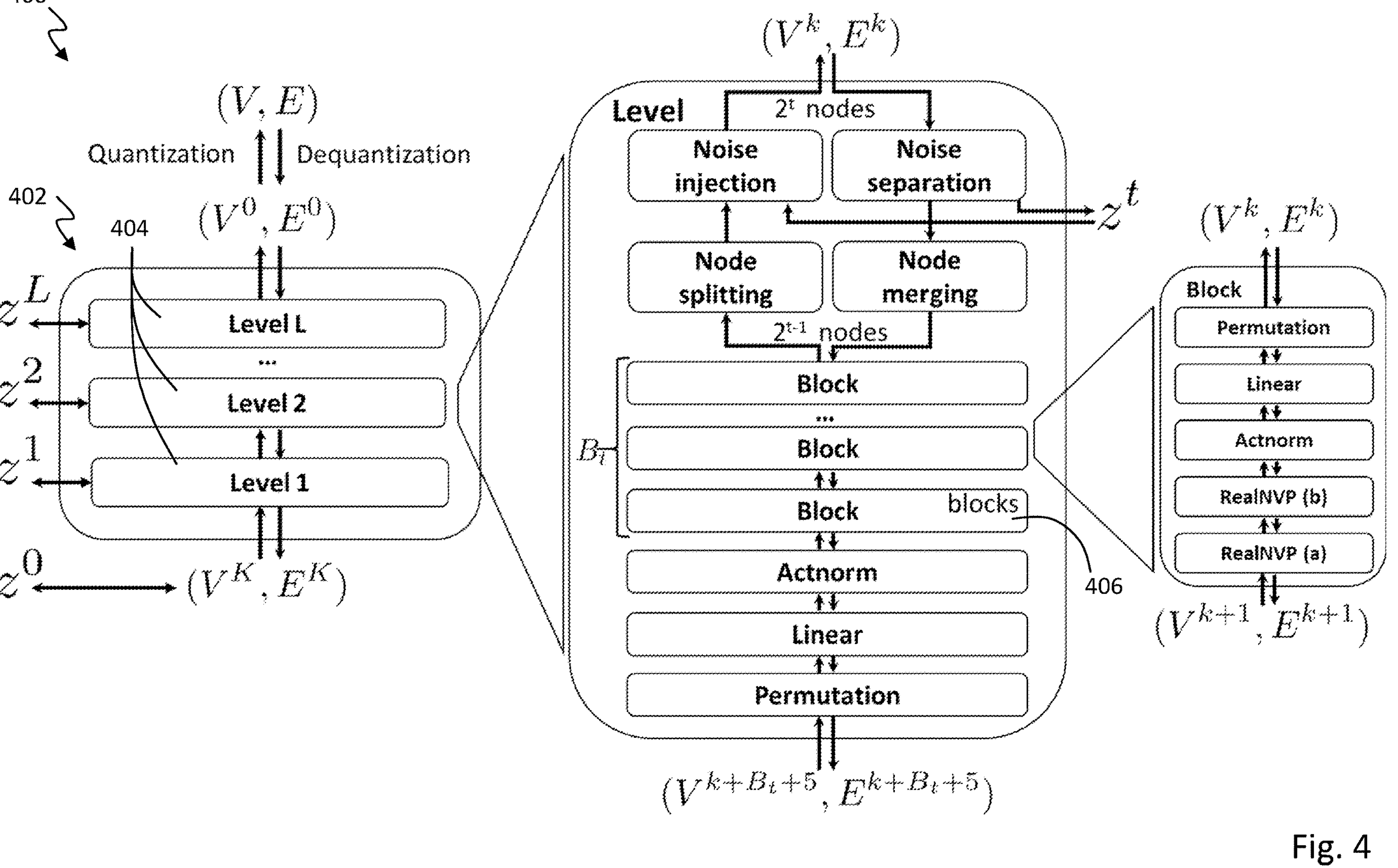
FIG. 4 shows an architecture for MolGrow.

FIG. 4 shows an architecture for MolGrow 400. The MolGrow 400 includes a full architecture having a latent code generator 402 (e.g., encoder). The latent code generator 402 includes multiple levels 404 as illustrated. Each level 404 can be configured for performing transformations on the data, which includes processing through various blocks 406. The blocks 406 each include three channel-wise transformations, such as permutation, linear (302), and actnorm (304). The blocks 406 also each include two RealNVP layers (306).

The full MolGrow 400 architecture combines multiple levels 404 to generate latent codes $z^L, \ldots, z^0$ from a graph (V,E) and vice versa. Each level 404 separates noise or applies noise injection in the inverse, merges node pairs or applies node splitting in the inverse, applies multiple blocks 406 and linear transformations (e.g., actnorm and inverse linear). Each block 406 applies three channel-wise transformations and two RealNVP layers. The channel-wise transformations include: permutation; linear, and Actnorm.

MolGrow 400 is a hierarchical normalizing flow model (generative model) that is configured to produce new molecular graphs from a single-node graph by recursively dividing every node into two nodes. The final graph has N=2L nodes, where L is the number of the node splitting layers in the model. To generate graphs with fewer nodes, the module can add special padding atoms to the molecular graph. The operator can choose N to be large enough to fit any graph from the training dataset.

We represent a graph with node attribute matrix V and edge attribute tensor E.

$V \in R^{N \times dv}$ $E \in R^{N \times N \times de}$

Here, $d_v$ and $d_e$ are feature dimensions. For the input data, $V_i$ defines atom type and charge, $E_{i,j}$ defines edge type. Since molecular graphs are non-oriented, the symmetry constraint is preserved on all intermediate layers: $E_{i,j,k}=E_{j,i,k}$.

MolGrow 400 includes L invertible levels 494. Each level 404 has its own latent code with a Gaussian prior. On a forward path, each level 404 extracts the latent code and halves the graph size by merging node pairs. On the inverse path, each level 404 does the opposite: it splits each node into two and adds additional noise. The final output on the forward path is a single-node graph and latent codes from each level: $z^L, \ldots, z^1$. The $z^0$ is a top level latent code. single-node graph: $z^0=(V^K, E^K)$.

In some embodiments, a dequantization protocol is performed. To avoid fitting discrete graphs into a continuous density model, the data is dequantized using a uniform noise [Durk P Kingma et al., Glow: Generative flow with invertible 1×1 convolutions. In *Advances in Neural Information Processing Systems*, pages 10215-10224, 2018.]. The dequantization is invertible and original data can be reconstructed by rounding down certain elements. The data can be dequantized for each training batch independently and train the model. The dequantized graph is a complete graph.

Figure 5A:
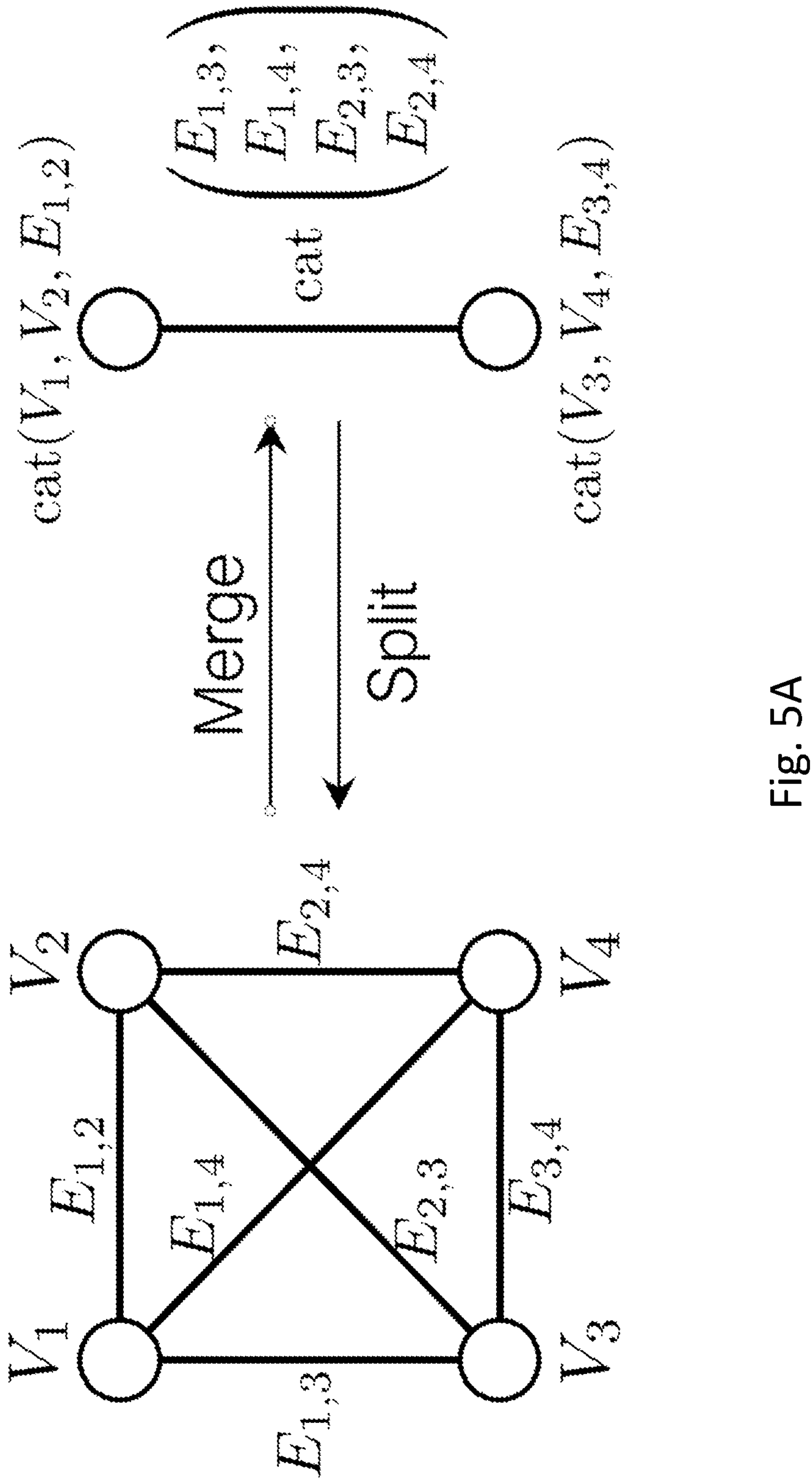
FIG. 5A illustrates a schematic of a node merging and splitting example for a 4-node graph.

In some embodiments, node merging and splitting is performed. The model can use node merging and splitting operations to control the graph size. These operations are inverse of each other, and both operate by rearranging node and edge features. Consider a graph with a number ofnodes. Node merging operation joins nodes 2i and 2i+1 into a single node by concatenating their features and features of the edge between them, such as concatenating the edge features connecting the merged nodes. Node splitting is the inverse of node merging layer: it slices features into original components. See an example in FIG. 5. FIG. 5 illustrates a schematic of a node merging and splitting example for a 4-node graph. The model concatenates features of nodes $V_1$ and $V_2$ and edge $E_{1,2}$ to get new node features. The model also concatenates edge features $E_{1,3}$, E1,4, E2,3, and E2,4. The splitting operation slices the merged graph's node and edge features.

In some embodiments, noise separation and injection is performed. MolGrow produces a latent vector for each level. The model derives the latent codes by separating half of the node and edge features before node merging and imposing a Gaussian prior on these latent codes. During generation, the model samples the latent code from the prior and concatenates it with node and edge features. As shown in the experiments, latent codes on different levels affect the generated structure (e.g., generated graph) differently. Latent codes from smaller intermediate graphs (top level) influence global structure, while bottom level have features that define local structure.

In some embodiments, the basic building block architecture in MolGrow (denoted as "block" in FIG. 1) consists of five layers. The first three layers (e.g., permutation layer, linear layer, and actnorm layer) serve as 1×1 convolutions. Each layer contains two transformations: one transforms every node and the other transforms every edge. The number of linear layer's Housholder reflections in matrix Q is smaller than the dimension of Q. Hence, a combination of linear and permutation layers is not equivalent to a single linear layer. For example, see FIG. 5 showing Algorithm 1.—Attention on complete graph edges (CAGE).

The final two layers of each block are RealNVP layers. RealNVP layer splits its input graph with nodes into A set and B set along features dimension. The B set can be transformed by projecting node and edge features onto a low-dimensional manifold and applying attention on complete graph edges (CAGE) architecture (Algorithm 1 of FIG. 5). The final output of RealNVP layer is computed by applying fully-connected neural networks to each node and edge independently.

Similar to other attentive graph convolutions [Petar Velickovic et al., Graph attention networks. *International Conference on Learning Representations*, 2017., Zhijiang Guo et al.,. Attention guided graph convolutional networks for relation extraction. In *Proceedings of the* 57th *Annual Meeting of the Association for Computational Linguistics*, pages 241-251, Florence, Italy, July 2019. Association for Computational Linguistics, CAGE architecture uses a multi-head attention [Ashish Vaswani et al., Attention is all you need. In *Advances in neural information processing systems*, pages 5998-6008, 2017]. It also uses gated recurrent unit update function to stabilize training [Emilio Parisotto et al., Stabilizing transformers for reinforcement learning. *Inter-*

*national Conference on Machine Learning,* 2020]. Positional encoding in CAGE consists of two parts. First dimensions are standard sinusoidal positional encoding. The last components of standard sinusoidal positional encoding contain a binary code. Multiple blocks are added before the first and after the last level in the full architecture.

Figure 7A:
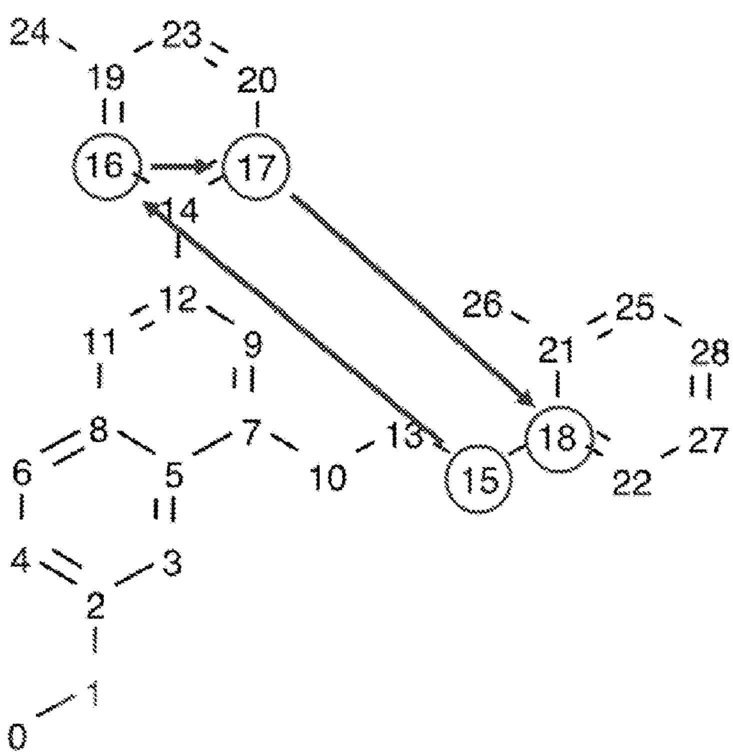
FIG. 7A shows the BFS ordering that is avoided with the present technology.

In some embodiments, the layout of the graph can be analyzed and balanced padding performed. The model has been used to achieved better results when learning on a fixed atom ordering, instead of learning a distribution over all permutations. Previous works used breadth-first search (BFS) atom ordering, since it avoids long-range dependencies. However, BFS does not incorporate the knowledge of common fragments and can mix their atoms (see FIG. 7A). FIG. 7A shows the BFS ordering that is avoided with the present technology. The proposed model described herein omits BFS. Instead, the proposed model uses a proposed new atom ordering to incorporate prior knowledge about frequent fragments. The proposed model ordering better organizes the latent space and simplifies generation, such as in FIG. 7B using the fragment-oriented ordering.

Figure 7B:
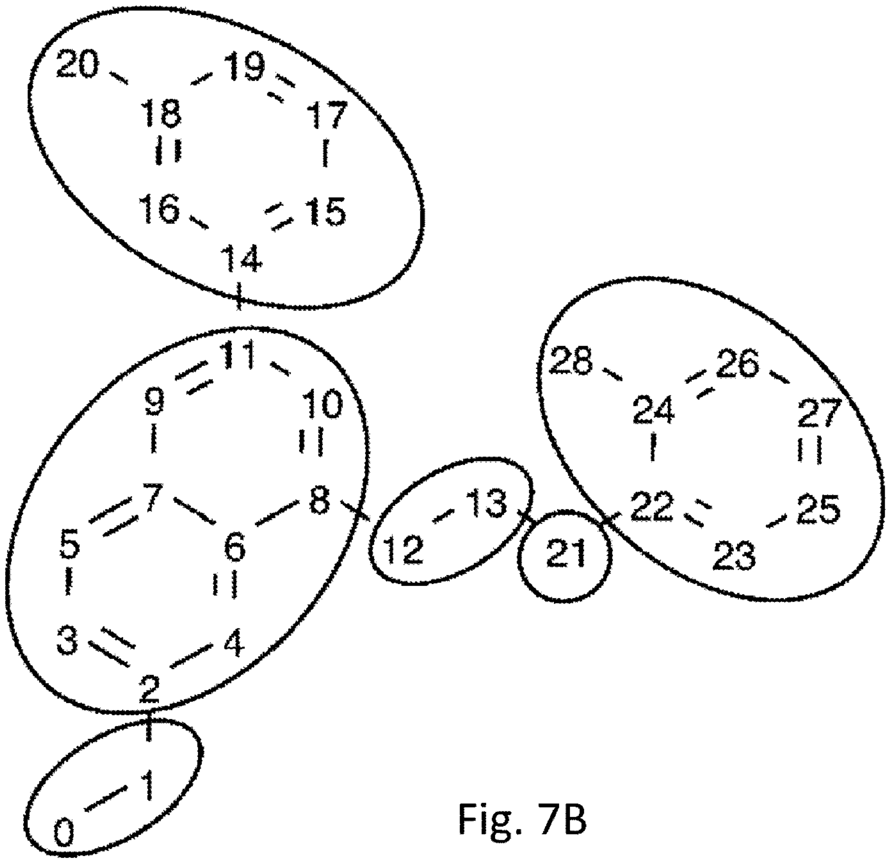
FIG. 7B shows the fragment-oriented ordering that is used with the present technology.

In FIGS. 7A-7B different atom orderings are used. Numbers are atom's indices in a particular ordering. Note that BFS ordering (FIG. 7A) generates two fragments in parallel (see nodes 15-18), while the present method completes a fragment before transitioning to the next one. For fragment-oriented ordering in FIG. 7B the extracted fragments are circled.

The method can break the molecule into fragments by removing BRICS [J Degen et al., On the art of compiling and using 'drug-like' chemical fragment spaces. *ChemMedChem,* 3(10):1503-1507, 2008.] bonds and bonds connecting rings, linkers, and decorations in the Bemis-Murcko scaffold [G W Bemis et al., The properties of known drugs. 1. molecular frameworks. *J. Med. Chem.,* 39(15):2887-2893, July 1996.]. The method then enumerates the fragments and atoms in each fragment using Fragment-Oriented Ordering (FOO) (FIG. 7B). The method then recursively choose padding positions, minimizing the number of edges after node merging layers (Algorithm 2 as shown in FIG. 8).

In some embodiments, a generative model can be used for the molecular generation task. By representing molecules as strings, one can apply any sequence generation model: language models [Marwin H S Segler et al., Generating focused molecule libraries for drug discovery with recurrent neural networks. *ACS Cent Sci*, 4(1): 120-131, January 2018.], variational autoencoders [Rafael Gomez-Bombarelli, et al., Automatic chemical design using a Data-Driven continuous representation of molecules. *ACS Central Science*, 4(2):268-276, February 2018.], and generative adversarial networks [Benjamin Sanchez-Lengeling et al., Optimizing distributions over molecular space. An Objective-Reinforced Generative Adversarial Network for Inverse-design Chemistry (ORGANIC). *ChemRxiv*, 8 2017. doi: 10.26434/chemrxiv.5309668.v3]. Molecular graphs satisfy a formal set of rules: all atoms must have a proper valency, and a graph must have only one component. These constraints can be learned implicitly from the data or explicitly by specifying grammar rules [Matt J Kusner et al.,. Grammar variational autoencoder. In *Proceedings of the* 34*th International Conference on Machine Learning-Volume* 70, pages 1945-1954. JMLR. org, 2017; Noel O'Boyle et al., DeepSMILES: An Adaptation of SMILES for Use in Machine-Learning of Chemical Structures. *ChemRxiv,* 2018; Mario Krenn et al., Selfies: a robust representation of semantically constrained graphs with an example application in chemistry. *arXiv preprint arXiv:* 1905.13741, 2019.].

Graph recurrent neural network (GraphRNN) and molecular recurrent neural network (MolecularRNN) use node and edge generators: node generator sequentially produces nodes; edge generator sequentially predicts edge types for all the previous nodes from the hidden states of a node generator. Molecular generative adversarial network (MolGAN) trains a critic on generated graphs and passes the gradient to the generator using deep deterministic policy gradient. Graph variational autoencoder (GraphVAE) encodes and decodes molecules using edge-conditioned graph convolutions. Graph autoregressive flow (GraphAF) iteratively produces nodes and edges; discrete one-hot vectors are dequantized, and tokens are decoded using argmax.

A graph non-volume preserving transformation (GraphNVP) model may also be used. GraphNVP generation is not autoregressive: the model produces a dequantized adjacency matrix using normalizing flow, turns it into a discrete set of edges by computing argmax, and obtains atom types using a normalizing flow. MoFlow exploits a two-stage graph generation process similar to GraphNVP: first, it generates an adjacency matrix with Glow architecture and then recovers node attributes with additional coupling layers. Unlike GraphNVP and MoFlow, the MolGrow described herein generate the graph hierarchically and inject noise on multiple levels. MolGrow also produces nodes and edges simultaneously.

The graph generative models mentioned above are not permutation invariant, and most of these models employ a fixed atom order. GraphVAE aligns generated and target graphs using Hungarian algorithm, but has high computational complexity. The order matters in set to set transformation problems with specific orderings giving better results. Most models learn on a breadth-first search (BFS) atom ordering. In BFS, new nodes are connected only to the nodes produced on the current or previous BFS layers, avoiding long range dependencies. Alternatively, graph generative models could use a canonical depth-first search (DFS) order.

In some embodiments, the hierarchical molecular graph generative model described herein outperforms existing node-level models on distribution learning and molecular property optimization tasks. On distribution learning, string- and fragment-based generators still perform better than node-level models, since they explicitly handle valency and connectivity constraints. Similar to the previous models, the hierarchical molecular graph generative model obtained better performance when learning on a fixed atom ordering. The present the hierarchical molecular graph generative model uses a fragment-oriented ordering that further improves the results over BFS methods. In this work, the generated and test sets were compared using standard distribution learning metrics, and it was found that the distributions produced by previous node-level graph generators differ significantly from the test set, although these models were trained for distribution learning.

In some embodiments, a computing method can be used for normalizing molecule graph data for hierarchical molecular generation. The method can include: providing a single-node molecule graph; recursively splitting every node into two nodes; perturbating a first layer of latent code to obtain a global structural change of at least one molecule; perturbating one or more consequent layers to change a resulting molecule in one or more changes to a scaffold or substituent of the at least one molecule; generating a generated molecular graph of a molecule; and providing a report with the generated molecular graph of the molecule.

In some embodiments, a computing method for normalizing molecule graph data for hierarchical molecular generation can be performed. The method can include: providing a molecule graph; and generating multiple levels of latent codes from the molecule graph. Each level separates noise, merges node pairs, and applies multiple blocks and linear transformations, wherein each block applies a plurality of channel-wise transformations and a plurality of nonlinear invertible transformations. The method can include performing a forward path for each level to extract a latent code and reduce graph size by merging node pairs; performing an inverse path for each level splits each node into two nodes and adds additional noise; and outputting a graph structure.

In some embodiments, the methods can include performing a dequantization comprising transforming a data distribution to a continuous domain by adding uniform noise to node and edge features.

In some embodiments, the method can include using node merging and node splitting to control size of the molecule graph.

In some embodiments, the method is performed with a block architecture comprising a building block of five layers comprising a permutation layer, linear layer, an activation normalization (actnorm) layer, and two real-valued non-volume preserving transformation (RealNVP) layers.

In some embodiments, the method is performed to include: transforming the molecule graph into nodes and edges; transforming the nodes and edges by projecting node and edge features onto a low-dimensional manifold; applying fully-connected neural networks to each node and edge independently; and performing an attentive graph convolution.

In some embodiments, the method can include performing a learning protocol on a fixed atom ordering of the molecule graph.

In some embodiments, the method can include: splitting the molecule graph into fragments; for each fragment, select the atom with a minimal breadth-first-search (BFS) index or a fragment-oriented ordering (FOO) index in the original molecule and sort the fragments according to indices; perform a BFS or FOO for selected atoms to order atoms in each fragment; obtain an ordered list of fragments and ordered list of atoms for each fragment; and concatenate the ordered list of fragments to obtain a final ordering.

In some embodiments, when the molecule of the generated graph has less than N atoms, the method can include inserting padding atoms in positions after a node merging. In some aspects, each fragment is covered by single intermediate node.

In some embodiments, a method of generating a molecule is provided. The method can include: performing a generative method to identify a molecular structure (e.g., generated graph); and synthesizing a real molecule to have the molecular structure of the generated graph. The methods can include performing analysis of the molecular structure to confirm the molecular structure, such as NMR, HPLS, etc. In some aspects, the methods can include performing a biological analysis to identify a bioactivity of the molecular structure.

In some embodiments, a computing method for normalizing molecule graph data for hierarchical molecular generation can include: providing a single-node molecule graph; recursively splitting every node into two nodes; perturbating a first layer of latent code to obtain a global structural change of at least one molecule; perturbating one or more consequent layers to change a resulting molecule in one or more changes to a scaffold or substituent of the at least one molecule; generating a generated molecular graph of a molecule; and providing a report with the generated molecular graph of the molecule.

In some embodiments, a computing method for normalizing molecule graph data for hierarchical molecular generation can include: providing a molecule graph; generating multiple levels of latent codes from the molecule graph, wherein each level separates: noise, merges node pairs, and applies multiple blocks and linear transformations, wherein each block applies a plurality of channel-wise transformations and a plurality of nonlinear invertible transformations; performing a forward path for each level to extract a latent code and reduce graph size by merging node pairs; performing an inverse path for each level splits each node into two nodes and adds additional noise; and outputting a one node graph.

In some embodiments, the methods can include performing a dequantization comprising transforming a data distribution to a continuous domain by adding uniform noise to node and edge features.

In some embodiments, the methods can include using node merging and node splitting to control size of the molecule graph.

In some embodiments, the method is performed with a block architecture comprising a building block of five layers comprising a permutation layer, linear layer, an activation normalization (actnorm) layer, and two real-valued non-volume preserving transformation (RealNVP) layers.

In some embodiments, the method can include: transforming the molecule graph into nodes and edges; transforming the nodes and edges by projecting node and edge features onto a low-dimensional manifold; applying fully-connected neural networks to each node and edge independently; and performing an attentive graph convolution. In some aspects, the method can include performing a learning protocol on a fixed atom ordering of the molecule graph.

In some embodiments, the method can include: splitting the molecule graph into fragments; for each fragment, select the atom with a minimal breadth-first-search (BFS) index in the original molecule and sort the fragments according to indices; perform a BFS for selected atoms to order atoms in each fragment; obtain an ordered list of fragments and ordered list of atoms for each fragment; and concatenate the ordered list of fragments to obtain a final ordering.

In some embodiments, when the generated molecule has less than N atoms, insert padding atoms in positions after a node merging, where each fragment is covered by single intermediate node.

In some embodiments, a method of generating a molecule can include: performing method to identify a molecular structure; and synthesizing a real molecule to have the molecular structure. The real molecule can then be validated (e.g., with NMR, HPLC, mass spectroscopy, etc.) to show it is the generated molecule.

Experimental

In the experiments, the methods are implemented to consider three problems: (1) distribution learning; (2) global molecular property optimization; and (3) constrained optimization. For all the experiments, the methods use model and optimization hyperparameters in supplementary material A; the source code for reproducing all the experiments is provided in supplementary materials. We consider hydrogen-depleted graphs, since hydrogens can be deduced from atom valence.

Distribution Learning

In a distribution learning task, the method assess how well models capture the data distribution. The method compares generated sets and a test sets using Frechet ChemNet distance (FCD/Test) [Kristina Preuer, et al., .Frechet ChemNet distance: A metric for generative models for molecules in drug discovery, *J. Chem. Inf. Model.*, 58(9):1736-1741, September 2018.]. The FCD/Test is a Wasserstein-1 distance between Gaussian approximations of ChemNet's penultimate layer activations. The method also computed cosine similarity between fragment frequency vectors in the generated and test sets. The method reports the results on MOSES [Daniil Polykovskiy et al., Molecular sets (MOSES): A benchmarking platform for molecular generation models. *Frontiers in Pharmacology,* 11:1931, 2020.] dataset in Table 1. MolGrow outperforms previous node-level graph generators by a large margin. Note that SMILES-based generators (CharRNN and VAE) and fragment-level generator (JTN-VAE) outperform all node-level graph models. It is thought that such representations impose strong prior on the generated structures. The method provides samples from graph-based models, as shown in MolGrow: A Graph Normalizing Flow for Hierarchical Molecular Generation, Maksim Kuznetsov, Daniil Polykovskiy, Insilico Medicine, Association for the Advancement of Artificial Intelligence (aaai.org;hse.ru/data/2021/03/16/1399050660/

Статья%203.pdf), incorporated herein by specific reference, where the graph generative models were trained on MOSES. Note that baseline models tend to produce macrocycles which were not present in the training set; molecules produced with GraphNVP contain too few rings. Ablation study demonstrates the advantage of fragment-oriented ordering and CAGE over standard graph attention network GAT.

considered genetic and predictor-guided optimization strategies.

For genetic optimization, the method starts by sampling 256 random molecules from ZINC250k dataset and computing their latent codes. Then the method hierarchically optimizes latent codes for 3000 iterations. At each iteration, the method generates a new population using crossing-over and mutation and keep 256 molecules with the highest reward. In crossing-over, the method randomly permutes all molecules in the population to form 256 pairs. For each pair, the model uniformly samples latent codes from spherical linear interpolation (Slerp) trajectory and reconstruct the resulting molecule. The method mutates one level's latent code at each iteration. Starting with a top level, the method resample 10% of the components from a Gaussian distribution. For genetic optimization, the method compares different mutation and crossing-over strategies, including top level optimization with fixed bottom layers and vice versa.

In predictor-guided optimization, the method can follow the approach proposed by Jin et al. [Wengong Jin et al.,. Junction tree variational autoencoder for molecular graph generation. In Jennifer Dy and Andreas Krause, editors, *Proceedings of the* 35*th International Conference on Machine Learning*, volume 80 of *Proceedings of Machine Learning Research*, pages 2323-2332, Stockholmsmassan, Stockholm Sweden, 2018. PMLR.]. The method fine-tuned the pre-trained model jointly with a penalized logP predictor from the high-level latent codes for one epoch (MAE=0.41 for penalized logP, MAE=0.07 for QED). The method randomly sampled 2560 molecules from a prior distribution and took 200 constrained gradient ascent steps along the predictor's gradient to modify the high-level latent codes. The method resamples low-level latent codes from the prior.

TABLE 1

| Method | FCD/Test (↓) | Frag/Test (↑) | Unique @ 10 k (↑) | Novelty (↑) |
|---|---|---|---|---|
| Graph-based models | | | | |
| MolecularRNN | 23.13 | 0.56 | 98.6% | 99.9% |
| GraphVAE | 49.39 | 0.0 | 5% | 100% |
| GraphNVP | 29.95 | 0.62 | 99.7% | 99.9% |
| GraphAF (BFS) | 21.84 | 0.651 | 97% | 99.9% |
| Proposed model | | | | |
| MolGrow (fragment-oriented) | 6.284 ± 0.986 | 0.9294 ± 0.025 | 99.28 ± 0.62% | 99.26 ± 0.12% |
| MolGrow (BFS) | 9.96 ± 0.795 | 0.933 ± 0.01 | 100 ± 0.0% | 99.4 ± 0.08% |
| MolGrow (BFS on fragments) | 16.1 ± 1.03 | 0.868 ± 0.02 | 100 ± 0.0% | 100 ± 0.0% |
| MolGrow (random permutation) | 40.2 ± 4.71 | 0.05 ± 0.04 | 59 ± 38.1% | 100 ± 0.0% |
| MolGrow (GAT instead of CAGE) | 6.52 ± 0.3 | 0.941 ± 0.013 | 99.4 ± 0.3% | 99.3 ± 0.06% |
| MolGrow (No positional embedding) | 6.77 ± 0.555 | 0.937 ± 0.006 | 99.5 ± 0.18% | 99.4 ± 0.06% |
| SMILES and fragment-based models | | | | |
| CharRNN (from MOSES benchmark) | 0.073 ± 0.024 | 0.9998 ± 0.000 | 99.73 ± 0.03% | 84.19 ± 5.09% |
| VAE (from MOSES benchmark) | 0.099 ± 0.012 | 0.9994 ± 0.000 | 99.84 ± 0.12% | 69.49 ± 0.69% |
| JTN-VAE (from MOSES benchmark) | 0.422 ± 0.023 | 0.9962 ± 0.000 | 100 ± 0.0% | 91.53 ± 0.58% |

The goal of a global optimization task is to produce new molecules that maximize a given chemical property. The method selected two commonly used properties: penalized octanol-water partition coefficient (penalized logP) and quantitative estimation of drug-likeness (QED). The method The method decreases the learning rate after each iteration and keeps the best reconstructed molecule that falls into the constrained region. Intuitively, the gradient ascent over high-level latent codes guides the search towards better global structure, while low-level latent codes produce a diverse set of molecules with the same global structure and similar predicted values. The method then reports the scores of the best molecules found during optimization, such as in Table 2. Table 2 shows the molecular property optimization: penalized octanol-water partition coefficient (penalized logP) and quantitative estimation of drug-likeness (QED).

TABLE 2

| | Penalized logP | | | QED | | |
|---|---|---|---|---|---|---|
| Method | 1st | 2nd | 3rd | 1st | 2nd | 3rd |
| Graph-based models | | | | | | |
| GCPN | 7.98 | 7.85 | 7.80 | 0.948 | 0.947 | 0.946 |
| MolecularRNN | 8.63 | 6.08 | 4.73 | 0.844 | 0.796 | 0.736 |
| GraphNVP | — | — | — | 0.833 | 0.723 | 0.706 |
| GraphAF | 12.23 | 11.29 | 11.05 | 0.948 | 0.948 | 0.948 |
| MoFlow | — | — | — | 0.948 | 0.948 | 0.948 |
| Proposed model | | | | | | |
| Genetic | 14.01 ± 0.36 | 13.95 ± 0.42 | 13.92 ± 0.42 | 0.948 ± 0.0 | 0.948 ± 0.0 | 0.948 ± 0.0 |
| Genetic, Top | 11.66 ± 0.31 | 11.65 ± 0.31 | 11.63 ± 0.31 | 0.948 ± 0.0 | 0.948 ± 0.0 | 0.948 ± 0.0 |
| Genetic, Bottom | 10.29 ± 3.32 | 10.29 ± 3.33 | 10.28 ± 3.32 | 0.948 ± 0.0 | 0.948 ± 0.0 | 0.948 ± 0.0 |
| Predictor-guided | 5.2 ± 0.34 | 4.94 ± 0.26 | 4.84 ± 0.22 | 0.948 ± 0.0 | 0.948 ± 0.0 | 0.948 ± 0.0 |
| REINFORCE | 4.81 ± 0.28 | 4.47 ± 0.14 | 4.39 ± 0.13 | 0.947 ± 0.001 | 0.946 ± 0.001 | 0.946 ± 0.001 |
| SMILES and fragment-based models | | | | | | |
| DD-VAE | 5.86 | 5.77 | 5.64 | — | — | — |
| Grammar VAE | 2.94 | 2.88 | 2.80 | — | — | — |
| SD-VAE | 4.04 | 3.50 | 2.96 | — | — | — |
| JT-VAE | 5.30 | 4.93 | 4.49 | 0.948 | 0.947 | 0.947 |

In some examples, constrained optimization is performed. As such, the method can apply MolGrow to constrained molecular optimization. In this task, the method optimizes a chemical property in proximity of the initial molecule. The method selected 800 molecules with the lowest penalized octanol-water partition coefficient (logP) and constrain minimum Tanimoto similarity 6 between Morgan fingerprints of the initial and final molecules. For constrained optimization, the method followed the predictor-guided approach described above and optimize each of 800 starting molecules for 200 steps. In Tables 3 and 4, it is reported that the average penalized logP improvement and similarity to the initial molecule. It is also reported that a fraction of molecules successfully discovered a new molecule with higher penalized logP. Note that unlike GCPN and GraphAF baselines, the method does not fine-tune the model for each starting molecule, reducing time and memory costs for optimization. Tables 3 and 4 show the constrained optimization of penalized octanol-water partition coefficient (logP).

TABLE 3

| | GCPN | | | GraphAF | | |
|---|---|---|---|---|---|---|
| δ | Improvement | Similarity | Success | Improvement | Similarity | Success |
| 0.0 | 4.20 ± 1.28 | 0.32 ± 0.12 | 100% | 13.13 ± 6.89 | 0.29 ± 0.15 | 100% |
| 0.2 | 4.12 ± 1.19 | 0.32 ± 0.11 | 100% | 11.90 ± 6.86 | 0.33 ± 0.12 | 100% |
| 0.4 | 2.49 ± 1.30 | 0.47 ± 0.08 | 100% | 8.21 ± 6.51 | 0.49 ± 0.09 | 99.88% |
| 0.6 | 0.79 ± 0.63 | 0.68 ± 0.08 | 100% | 4.98 ± 6.49 | 0.66 ± 0.05 | 96.88% |

| | MoFlow | | | MolGrow | | |
|---|---|---|---|---|---|---|
| δ | Improvement | Similarity | Success | Improvement | Similarity | Success |
| 0.0 | 8.61 ± 5.44 | 0.30 ± 0.20 | 98.88% | 14.84 ± 5.786 | 0.048 ± 0.038 | 100% |
| 0.2 | 7.06 ± 5.04 | 0.43 ± 0.20 | 96.75% | 11.99 ± 6.45 | 0.23 ± 0.045 | 99.88% |
| 0.4 | 4.71 ± 4.55 | 0.61 ± 0.18 | 85.75% | 8.337 ± 6.85 | 0.44 ± 0.048 | 99.88% |
| 0.6 | 2.10 ± 2.86 | 0.79 ± 0.14 | 58.25% | 4.063 ± 5.609 | 0.65 ± 0.068 | 97.78% |

Computations

Normalizing Flows Module

Normalizing flows are generative models that transform a prior distribution p(z) into a target distribution p(x) by composing invertible functions $f_k$:

$$z = f_K \circ \ldots \circ f_2 \circ f_1(x) \tag{1}$$

$$x = f_1^{-1} \circ \ldots \circ f_{K-1}^{-1} \circ f_K^{-1}(z) \tag{2}$$

Equation 1 is a forward path, and Equation 2 is an inverse path. The prior distribution p(z) is often a standard multivariate normal distribution N(0,I). Such models are trained by maximizing training set log-likelihood using the change of variables formula:

$$\log p(x) = \log p(z) + \sum_{i=1}^{K} \log\left|\det\left(\frac{dh_i}{dh_{i-1}}\right)\right| \tag{3}$$

In Equation 3:

$h_i = f_i(h_{i-1}),\ h_0 = x.$

To efficiently train the model and sample from it, inverse transformations and Jacobian determinants should be tractable and computationally efficient. In this work, we consider three types of layers: invertible linear layer, actnorm, and real-valued non-volume preserving transformation (RealNVP) [Laurent Dinh, Jascha Sohl-Dickstein, and Samy Bengio. Density estimation using real nvp. *International Conference on Learning Representations*, 2017]. We define these layers below for arbitrary d-dimensional vectors, and extend these layers for graph-structured data in the next section.

We consider an invertible linear layer parameterization by Hoogeboom et al. [Emiel Hoogeboom et al., Emerging convolutions for generative normalizing flows. *Proceedings of the* 36*th International Conference on Machine Learning*, volume 97 of *Proceedings of Machine Learning Research*, pages 2771-2780, Long Beach, Calif., USA, 09-15 Jun. 2019. PMLR.] that uses QR decomposition of a weight matrix: h=QR·z, where Q is an orthogonal matrix ($Q^T=Q^{-1}$), and R is an upper triangular matrix with ones on the main diagonal. We use Householder reflections to parameterize Q:

$$Q = \prod_{i=1}^{d'} \left(I - 2\frac{v_i v_i^T}{|v_i|^2}\right) \tag{4}$$

In Equation 4, where $v_i$ are learnable column-vectors. The Jacobian determinant of a linear layer is 1. QR decomposition showed more numerically stable results that prior methods.

The Actnorm layer [Durk P Kingma et al., Glow: Generative flow with invertible 1×1 convolutions. In *Advances in Neural Information Processing Systems*, pages 10215-10224, 2018.] is a linear layer with a diagonal weight matrix: h=s ⊙ z+m, where ⊙ is an element-wise multiplication. Vectors s and m are initialized so that the output activations from this layer have zero mean and unit variance at the beginning of training. We use the first training batch for initialization. The Jacobian determinant of this layer is $$\prod_{i=1}^{d} s_i.$$

RealNVP layer [Laurent Dinh et al., Density estimation using real nvp. *International Conference on Learning Representations*, 2017.] is a nonlinear invertible transformation. Consider a vector z of length d=2t with first half of the components denoted as $z_a$, and the second half as $z_b$. Then, RealNVP and its inverse transformations are:

$$\begin{pmatrix} h_a \\ h_b \end{pmatrix} = \begin{pmatrix} z_b \\ e^{s_\theta(z_b)} \odot z_a + t_\theta(z_b) \end{pmatrix} \tag{5}$$

$$\begin{pmatrix} z_a \\ z_b \end{pmatrix} = \begin{pmatrix} (h_b - t_\theta(h_a))/e^{s_\theta(h_a)} \\ h_a \end{pmatrix} \tag{6}$$

Functions $S_\theta$ and $t_\theta$ do not have to be invertible, and usually take form of a neural network. The Jacobian determinant of the RealNVP layer is $$\prod_{i=1}^{d} e^{S_{\theta,i}(z_b)}.$$

We sequentially apply two RealNVP layers to transform both components of z. We also use permutation layer that deterministically shuffles input dimensions before RealNVP—this is equivalent to randomly splitting data into a and b parts Dequantization To avoid fitting discrete graphs into a continuous density model, we dequantize the data using a uniform noise [Durk P Kingma et al.,. Glow: Generative flow with invertible 1×1 convolutions. In *Advances in Neural Information Processing Systems*, pages 10215-10224, 2018.]:

$$V_{i,j}^0 = V_{i,j} + u_{i,j}^v \tag{7}$$

$$E_{i,j,k}^0 = E_{j,i,k}^0 = \begin{cases} E_{i,j,k} + u_{i,j,k}^e, & i < j \\ 0, & i = j \end{cases} \tag{8}$$

Elements of $u^v$ and $u^e$ are independent samples from a uniform distribution $\mathcal{U}$ [0, c]. Such dequantization is invertible for c ∈ [0,1)—original data can be reconstructed by rounding down the elements of $$V_{i,j}^0 \text{ and } E_{i,j,k}^0.$$

We dequantize the data for each training batch independently and train the model on ($V^0$, $E^0$). Dequantizated graph ($V^0$, $E^0$) is a complete graph.

Node Merging and Splitting

We use node merging and splitting operations to control the graph size. These operations are inverse of each other, and both operate by rearranging node and edge features. Consider a graph ($V^k$, $E^k$) with $N_k$ nodes. Node merging operation joins nodes 2i and 2i+1 into a single node by concatenating their features and features of the edge between them. We concatenate edge features connecting the merged nodes:

$$\underbrace{V_i^{k+1}}_{2d_v+d_e} = cat\left(\underbrace{V_{2i}^k}_{d_v}, \underbrace{V_{2i+1}^k}_{d_v}, \underbrace{E_{2i,2i+1}^k}_{d_e}\right) \tag{9}$$

$$\underbrace{E_{i,j}^{k+1}}_{4d_e} = cat\left(\underbrace{E_{2i,2j}^k}_{d_e} \underbrace{E_{2i,2j+1}^k}_{d_e}, \underbrace{E_{2i+1,2j}^k}_{d_e}, \underbrace{E_{2i+1,2j+1}^k}_{d_e}\right) \tag{10}$$

Node splitting is the inverse of node merging layer: it slices features into original components. See an example in FIG. 5.

Block Architecture

The basic building block in MolGrow (denoted block in FIG. 4) consists of five layers. The first three layers (permutation, linear, and actnorm) serve as 1×1 convolutions. Each layer contains two transformations: one transforms every node and the other transforms every edge. The number of linear layer's Housholder reflections in matrix Q is smaller than the dimension of Q. Hence, a combination of linear and permutation layers is not equivalent to a single linear layer.

The final two layers of the block are RealNVP layers. RealNVP layer splits its input graph ($V^k$, $E^k$) with $N_k$ nodes into ($V^{k,a}$, $E^{k,a}$)and ($V^{k,b}$, $E^{k,b}$)along features dimension. We transform ($V^{k,b}$, $E^{k,b}$) by projecting node and edge features onto a low-dimensional manifold and applying attention on complete graph edges (CAGE) architecture (Algorithm 1-FIG. 5). We compute the final output of RealNVP layer by applying fully-connected neural networks $$s_\theta^v, t_\theta^v, s_\theta^e, \text{ and } t_\theta^e$$

to each node and edge independently:

$$(\overline{V}^{k,b}, \overline{E}^{k,b}) = \text{CAGE}(V^{k,b}W_v, E^{k,b}W_e) \tag{11}$$

$$V_i^{k+1,b} = \exp(s_\theta^v(\overline{V}_i^{k,b})) \odot V_i^{k,a} + t_\theta^v(\overline{V}_i^{k,b}) \tag{12}$$

$$V_i^{k+1,a} = V_i^{k,b} \tag{13}$$

$$E_{i,j}^{k+1,b} = \exp(s_\theta^e(\overline{E}_{i,j}^{k,b})) \odot E_{i,j}^{k,a} + t_\theta^e(\overline{E}_{i,j}^{k,b}) \tag{14}$$

$$E_{i,j}^{k+1,a} = E_{i,j}^{k,b} \tag{15}$$

CAGE architecture uses a multi-head attention [Ashish Vaswani et al., Attention is all you need. In *Advances in neural information processing systems,* pages 5998-6008, 2017.]. It also uses gated recurrent unit update function to stabilize training [Emilio Parisotto et al. Stabilizing transformers for reinforcement learning. *International Conference on Machine Learning,* 2020.]. Positional encoding in CAGE consists of two parts. First $d_v$—[$\log_2 N_k$] dimensions are standard sinusoidal positional encoding:

$$\text{pos}_{i,2j}=\sin(i/10000^{2j/d_v}) \tag{15}$$

$$\text{pos}_{i,2j+1}=\cos(i/10000^{2j/d_v}) \tag{16}$$

The last [$\log_2 N_k$] components of $\text{POS}_i$ contain a binary code of i. We add multiple blocks before the first and after the last level in the full architecture.

Hyperparameters

MolGrow model has 6 steps for ZINC250K dataset, 5 steps for MOSES dataset, and 4 steps for QM9 dataset. Each step contains 2 blocks if its input graph contains at most 16 nodes, and 4 blocks otherwise. We apply additional 4 blocks to the initial one-node latent codes.

CAGE projects node and edge feature vectors onto a 64 dimensional manifold; the number of attention heads equals 16. Neural networks $s^v_\theta$, $t^v_\theta$, $s^e_\theta$, and $t^e_\theta$ are 2-layer fully-connected neural networks with ReLU activations. The hidden size of these networks is 4 times bigger than the output size. The final layer of $s^e_\theta$ and $s^v_\theta$ is a sigmoid function.

In QR decomposition for linear layers we parameterize matrix Q decomposition with 128 Householder reflections. We sample $v_i$ from N(0,I) and normalize them. We re-normalize $v_i$ after each model optimization step. We initialize matrix R with elements from N(0,0.05*I) above diagonal; zeros below the diagonal, and ones on diagonal.

We train the model with Adam optimizer with learning rate 0.001 which decreases by a factor of 0.8 after each training epoch for MOSES, and by a factor of 0.92 after each training epoch for QM9 and ZINC250K datasets. The batch size is 256 for MOSES and QM9 datasets, and 80 for ZINC250K datasets. We train the model for 10 epochs on MOSES and 30 epochs on ZINC250k and QM9.

In our experiments we used QM9, ZINC250k, and MOSES datasets. For QM9 we use N=16 nodes with $d_v$=6 atom types, including padding atom type. For MOSES we used N=32 nodes with $d_v$=9 atom types, and N=64 with $d_v$=14 (11 for atom types and 3 for charge type) and for ZINC250K. The number of bond types is $d_e$=4 (none, single, double, triple).

We sample the latent codes from a multivariate normal distribution N(0,I) and multiply them by a temperature parameter 0.7.

We performed a hyperparameter search on the number of blocks in each level (considered 2,4,8,16 blocks) and internal shape of CAGE (considered 8,16,32,64 elements in hidden layer). The best hyperparameters are described above. To train MolGrow on one dataset we used Tesla K80 GPU. The training procedure took approximately 2 days for each dataset.

Distribution Learning

For distribution learning, we provide additional experiments on QM9 and ZINC250k datasets (Table 5 and Table 6). To compute validity for MolGrow, we removed edges that exceed maximum atom valency. If a final graph contains more than one fragment, we keep only the biggest one. Validity without cleanup corresponds to a fraction of valid molecules when no additional manipulations are performed on the generated graph. We check validity using RDKit and additionally consider molecules with multiple components invalid. We can provide reports with property distribution plots for models trained on MOSES.

TABLE 5

| Method | Validity | Validity without cleanup | Unique @ 10 k | Novelty | Reconstruction |
|---|---|---|---|---|---|
| JT-VAE | 100% | — | 100% | 100% | 76.7% |
| MolecularRNN | 100% | 65% | 99.89% | 100% | — |
| GraphNVP | 42.6% | — | 94.8% | 100% | 100% |
| GraphAF | 100% | 68% | 99.1% | 100% | 100% |
| MoFlow | 100 ± 0.0% | 81.76 ± 0.21% | 99.99 ± 0.01% | 100 ± 0.0% | 100 ± 0.0% |
| MolGrow | 100 ± 0.0% | 57.8 ± 7.75% | 99.06 ± 0.46% | 99.96 ± 0.01% | 100 ± 0.0% |

TABLE 6

| Method | Validity | Validity without cleanup | Unique @ 10 k | Novelty | Reconstruction |
|---|---|---|---|---|---|
| GraphVAE | — | 55% | 76% | 61% | 55% |
| GraphNVP | 83% | — | 99.2% | 58.2% | 100% |
| GraphAF | 100% | 67% | 94.5% | 88.8% | 100% |
| MoFlow | 100 ± 0.0% | 96.17 ± 0.18% | 99.20 ± 0.12% | 98.03 ± 0.14% | 100 ± 0.0% |
| MolGrow | 100 ± 0.0% | 86.80 ± 0.12% | 99.15 ± 0.05% | 81.43 ± 0.53% | 100 ± 0.0% |

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In one embodiment, the present methods can include aspects performed on a computing system. As such, the computing system can include a memory device that has the computer-executable instructions for performing the method. The computer-executable instructions can be part of a computer program product that includes one or more algorithms for performing any of the methods of any of the claims.

In one embodiment, any of the operations, processes, methods, or steps described herein can be implemented as computer-readable instructions stored on a computer-readable medium. The computer-readable instructions can be executed by a processor of a wide range of computing systems from desktop computing systems, portable computing systems, tablet computing systems, hand-held computing systems as well as network elements, base stations, femtocells, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those generally found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Figure 6:
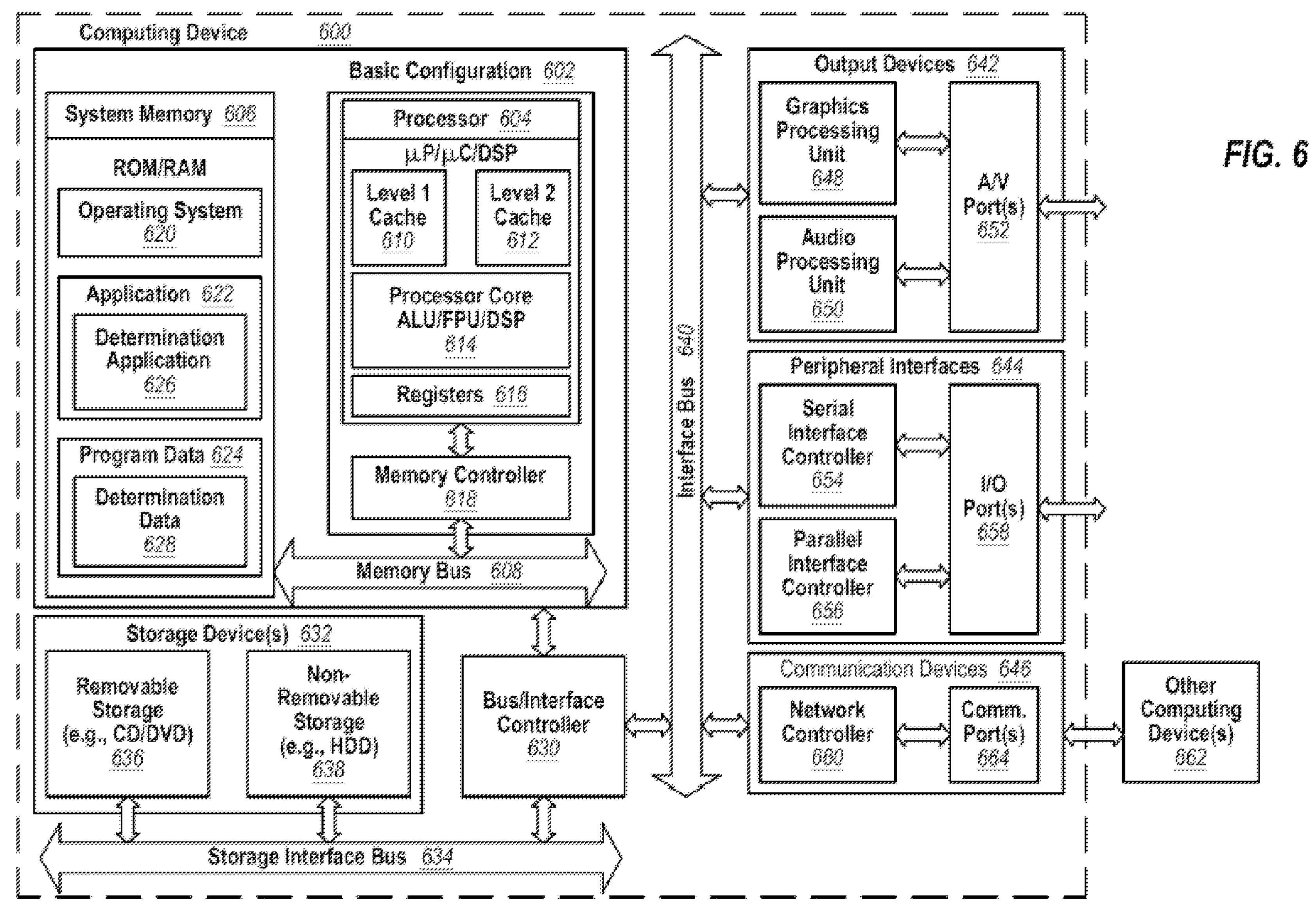
FIG. 6 illustrates an embodiment of a computing system that can be used to perform the methods described herein.

FIG. 6 shows an example computing device 600 that is arranged to perform any of the computing methods described herein. In a very basic configuration 602, computing device 600 generally includes one or more processors 604 and a system memory 606. A memory bus 608 may be used for communicating between processor 604 and system memory 606.

Depending on the desired configuration, processor 604 may be of any type including but not limited to a microprocessor (μP), a microcontroller (μC), a digital signal processor (DSP), or any combination thereof. Processor 604 may include one more levels of caching, such as a level one cache 610 and a level two cache 612, a processor core 614, and registers 616. An example processor core 614 may include an arithmetic logic unit (ALU), a floating point unit (FPU), a digital signal processing core (DSP Core), or any combination thereof. An example memory controller 618 may also be used with processor 604, or in some implementations memory controller 618 may be an internal part of processor 604.

Depending on the desired configuration, system memory 606 may be of any type including but not limited to volatile memory (such as RAM), non-volatile memory (such as ROM, flash memory, etc.) or any combination thereof. System memory 606 may include an operating system 620, one or more applications 622, and program data 624. Application 622 may include a determination application 626 that is arranged to perform the functions as described herein including those described with respect to methods described herein. Program Data 624 may include determination information 628 that may be useful for analyzing the contamination characteristics provided by the sensor unit 240. In some embodiments, application 622 may be arranged to operate with program data 624 on operating system 620 such that the work performed by untrusted computing nodes can be verified as described herein. This described basic configuration 602 is illustrated in FIG. 6 by those components within the inner dashed line.

Computing device 600 may have additional features or functionality, and additional interfaces to facilitate communications between basic configuration 602 and any required devices and interfaces. For example, a bus/interface controller 630 may be used to facilitate communications between basic configuration 602 and one or more data storage devices 632 via a storage interface bus 634. Data storage devices 632 may be removable storage devices 636, non-removable storage devices 638, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 606, removable storage devices 636 and non-removable storage devices 638 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 600. Any such computer storage media may be part of computing device 600.

Computing device 600 may also include an interface bus 640 for facilitating communication from various interface devices (e.g., output devices 642, peripheral interfaces 644, and communication devices 646) to basic configuration 602 via bus/interface controller 630. Example output devices 642 include a graphics processing unit 648 and an audio processing unit 650, which may be configured to communicate to various external devices such as a display or speakers via one or more A/V ports 652. Example peripheral interfaces 644 include a serial interface controller 654 or a parallel interface controller 656, which may be configured to communicate with external devices such as input devices (e.g., keyboard, mouse, pen, voice input device, touch input device, etc.) or other peripheral devices (e.g., printer, scanner, etc.) via one or more I/O ports 658. An example communication device 646 includes a network controller 660, which may be arranged to facilitate communications with one or more other computing devices 662 over a network communication link via one or more communication ports 664.

The network communication link may be one example of a communication media. Communication media may generally be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 600 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 600 may also be implemented as a personal computer including both laptop computer and non-laptop computer configurations. The computing device 600 can also be any type of network computing device. The computing device 600 can also be an automated system as described herein.

The embodiments described herein may include the use of a special purpose or general-purpose computer including various computer hardware or software modules.

Embodiments within the scope of the present invention also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media.

Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the term "module" or "component" can refer to software objects or routines that execute on the computing system. The different components, modules, engines, and services described herein may be implemented as objects or processes that execute on the computing system (e.g., as separate threads). While the system and methods described herein are preferably implemented in software, implementations in hardware or a combination of software and hardware are also possible and contemplated. In this description, a "computing entity" may be any computing system as previously defined herein, or any module or combination of modulates running on a computing system.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety.

The invention claimed is:

1. A method for normalizing molecular graph data for hierarchical molecular generation, the method comprising:

providing molecular graph data of at least one molecule having a node into a computing system, the at least one molecule having a given chemical property of a real molecule;

recursively splitting the node into two nodes with the computing system;

iteratively recursively splitting other nodes in the molecular graph data into two nodes with the computing system to obtain generated molecules, wherein each iteration of node splitting is performed by respective node splitting layer;

generating generated molecular graph data of a generated molecule of the generated molecules from node splitting with the computing system, the generated molecule having 2*L nodes, in which L represents a number of node splitting layers used; and synthesizing a real molecule having a molecular structure of the generated molecule.

2. The method of claim 1, comprising iteratively merging two nodes into a single node with the computing system.

3. The method of claim 1, comprising perturbating a first layer of latent code to obtain a global structural change of at least one resulting molecule of the generated molecular graph with the computing system.

4. The method of claim 3, comprising perturbating one or more consequent layers to change at least one resulting molecule in one or more changes to a scaffold or substituent of the at least one resulting molecule to obtain a generated molecular graph with the computing system.

5. The method of claim 1, wherein the molecular graph data includes a single node graph data, and the generated molecular graph includes a multi node graph data.

6. The method of claim 1, comprising performing a fragment-oriented atom ordering that improves hierarchical normalizing flow of a model over breadth-first search ordering with the computing system.

7. The method of claim 1, comprising mapping a molecular structure of the molecular graph data onto a fixed-sized hierarchical manifold with the computing system.

8. The method of claim 1, comprising transforming a prior distribution into a target distribution through invertible functions having a forward path and an inverse path with the computing system.

9. The method of claim 8, wherein:

the prior distribution is a standard multivariate normal distribution of the molecular graph data; and the target distribution includes the generated molecular graph data.

10. The method of claim 1, comprising performing the following with the computing system:

processing the molecular graph data through a plurality of levels of operations to generate latent codes in each level of operations in a forward path and/or an inverse path;

each level of operations performs a sequence of sublevels of operations in a forward path and an inverse path, wherein the sublevels of operations include at least: noise injection operation;

noise separation operation; a node merging operation; a node splitting operation; a plurality of block operations; actnorm transformation; linear transformation; and permutation transformation; and each sublevel of operations performs a sequence of operations in a forward path and an inverse path, each block operation includes at least: permutation transformation; linear transformation; actnorm transformation; first real-valued non-volume preserving transformation;

and second real-valued non-volume preserving transformation.

11. The method of claim 10, wherein for at least one of the sublevels of operation or each block operation:

the linear transformation includes an invertible linear transformation, and a decomposition of a weight matrix with an orthogonal matrix and upper triangular matrix with ones on the main diagonal;

the actnorm transformation includes a linear transformation with a diagonal weight matrix;

the first and second real-valued non-volume preserving transformation are sequentially applied as nonlinear invertible transformations; and the permutation transformation deterministically shuffles input dimensions or randomly splits data into two separate parts.

12. The method of claim 11, wherein:

each forward path of each of the levels extracts the latent code and halves its graph size by merging node pairs; and each inverse path of each of the levels splits each node into two nodes and adds additional noise.

13. The method of claim 12, wherein the forward path provides output as a single node graph and latent codes for each level.

14. The method of claim 12, further comprising performing a dequantization with uniform noise, wherein data for a training batch is independently dequantized to obtain a complete graph, and a model is trained on the complete graph with the computing system.

15. The method of claim 12, further comprising producing a latent vector for each level with the computing system by:

deriving latent codes by separating half of node and edge features before node merging;

imposing a Gaussian prior on the derived latent codes; and sampling a derived latent code of the derived latent codes from the Gaussian prior and concatenating the latent code with node and edge features.

16. The method of claim 1, wherein the method is performed in a distribution learning and property optimization task.

17. The method of claim 16, comprising providing a report that includes distribution learning metrics or graph generative models.

18. The method of claim 1, comprising using node merging and node splitting to control size of the generated molecular graph.

19. The method of claim 1, comprising performing the following with the computing system:

transforming the molecular graph into nodes and edges;

transforming the nodes and edges by projecting node and edge features onto a low-dimensional manifold;

applying fully-connected neural networks to each node and edge independently; and performing an attentive graph convolution.

20. The method of claim 1, comprising performing the following with the computing system:

splitting the molecule graph into fragments;

for each fragment, selecting an atom with a minimal breadth-first-search (BFS) index in an original molecule and sorting the fragments according to indices;

performing a BFS for selected atoms to order atoms in each fragment;

obtaining an ordered list of fragments and ordered list of atoms for each fragment; and concatenating the ordered list of fragments to obtain a final ordering.

21. The method of claim 1, further comprising validating the real molecule to be a physical version of the generated molecule.

* * * * *